(12) United States Patent
Sardaryan

(10) Patent No.: US 7,214,713 B2
(45) Date of Patent: May 8, 2007

(54) ANTRAQUINONE COMPOSITIONS AS ANTICANCER COMPOSITIONS AND NUTRITION SUPPLEMENTS AND METHODS OF MAKING AND USING THEM

(76) Inventor: Eduard Sardaryan, Sakarova 1386, 530 09 Pardubice (CZ)

( * ) Notice: Subject to any disclaimer, the term of this patent is extended or adjusted under 35 U.S.C. 154(b) by 593 days.

(21) Appl. No.: 10/344,567

(22) PCT Filed: Jul. 23, 2001

(86) PCT No.: PCT/CZ01/00039

§ 371 (c)(1),
(2), (4) Date: Feb. 12, 2003

(87) PCT Pub. No.: WO02/11563

PCT Pub. Date: Feb. 14, 2002

(65) Prior Publication Data

US 2004/0105864 A1    Jun. 3, 2004

(30) Foreign Application Priority Data

Aug. 10, 2000    (CZ) ................... 2000-2950

(51) Int. Cl.
*A61K 31/19*  (2006.01)
*C07C 45/27*  (2006.01)
*C07C 50/18*  (2006.01)

(52) U.S. Cl. .................... 514/570; 552/208
(58) Field of Classification Search ............... 552/208; 514/570
See application file for complete search history.

(56) References Cited

U.S. PATENT DOCUMENTS 5,264,235 A * 11/1993 Duckworth ............. 426/589
5,789,602 A    8/1998 Tabata et al. ............. 549/299

FOREIGN PATENT DOCUMENTS

WO    WO 99/50434    10/1999
WO    WO9950434   * 10/1999    ........... 552/208

OTHER PUBLICATIONS

Carter et al, Chemotherapy of Caner 2nd Ed, 1981, pp. 362-365.*
Ockerman, Food Science Sourcebook, Van Nostrand Reinhold, 1991, 2nd Edition, Part 1, p. 449.*
Sevcik et al., Czech J. Food Sci., 2000, Ceska Akademie Zemedelskych Ved, vol. 18, pp. 224-225.*
Patent Abstracts of Japan, vol. 018, No. 680, Dec. 21, 1994 and JP 06271561 (Sep. 27, 1994) [Abstract].

* cited by examiner

*Primary Examiner*—San-Ming Hui
(74) *Attorney, Agent, or Firm*—Morrison & Foerster LLP

(57) ABSTRACT

A food supplement having prophylactic and-cancer effects, wherein the supplement comprises 20 to 99.99% by weight of a product of biosynthesis by the productive microorganism Penicillium oxalicum var. Armeniaca CCM 8242, obtained by fermentation of a nutrient broth containing carbohydrates and ammonia nitrogen, and 0.01 to 8'% by weight of a physiologically inert carrier, and optionally auxiliary additives.

45 Claims, 1 Drawing Sheet

ANTRAQUINONE COMPOSITIONS AS ANTICANCER COMPOSITIONS AND NUTRITION SUPPLEMENTS AND METHODS OF MAKING AND USING THEM

This application is a U.S. National Phase Patent Application of PCT/CZ01/00039, filed Jul. 23, 2001, and claims benefit of priority under 35 U.S.C. 119 from PV 2000-2950, filed Aug. 10, 2000, which is hereby incorporated by reference as if fully set forth.

TECHNICAL FIELD

The invention relates to a food supplement having prophylactic anti-cancer effects.

BACKGROUND ART

There have been known various food supplements for supplementing nutrition, especially human nutrition, having beneficiary effects on the health condition, optionally inhibitory effects to emergence of certain diseases.

Czech patent No. 285 721 (WO 99/50434) describes the strain of the microorganism *Penicillium oxalicum* var. *Armeniaca* CCM 8242, producing a red colorant, and use of said colorant as, inter alia, a food colorant. The strain was deposited at the International Depositary Authority CCM—Czech Collection of Microorganisms of The Masaryk University, Tvrdého 14, 602 00 Brno, Czech Republic, on 19 Mar. 1998. It is a natural microorganism, obtained from the soil in a valley below the Ararat Mountain.

DISCLOSURE OF THE INVENTION

It has now been found that the product obtained by biosynthesis by the productive microorganism *Penicillium oxalicum* var. Armeniaca CCM 8242, when used in food supplements, confers anti-cancer effects to said supplements.

Accordingly, the invention consists in a food supplement having prophylactic anti-cancer effects, wherein the supplements comprises 20 to 99.99% by weight of a product of biosynthesis by the productive microorganism *Penicillium oxalicum* var. Armeniaca CCM 8242, obtained by fermentation of a nutrient broth containing carbohydrates and ammonia nitrogen, and 0.01 to 80% by weight of a physiologically inert carrier, and optionally auxiliary additives. In one aspect, the carrier comprises 11 to 75 weight % maltodextrin, or, the carrier comprises 30 to 40 weight % starch.

In order to obtain the product of biosynthesis, it is possible to cultivate the productive strain by common fermentation processes. When the red colorant, obtained by isolating methods from the cultivated aqueous medium after separation of the biomass, was subjected to spectral analysis, it has been found that it, while having the dry matter content not less than 85% by weight, contains not less than 52% by weight of coloured substances.

The colouring principle is based on a chromophore of the anthraquinone type. The colorant is composed of a mixture of substances which contain said chromophore and which differ from the basic structure in pending side-chains of oligopeptides or oligosaccharides.

The chromophore itself is a penta-substituted anthraquinone having three isolated skeletal hydrogens. Such compound can be depicted, for example, by general formula I

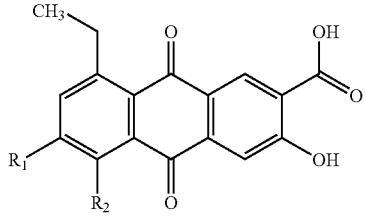

wherein $R_1$ is hydroxy and $R_2$ is 3-methyl-1,3-butadienyl, and-optionally $R_1$ and $R_2$ are cyclized together through the oxygen atom of the hydroxy.

Thus, formula Ia corresponds to the basic variant and formula Ib corresponds to the cyclized one.

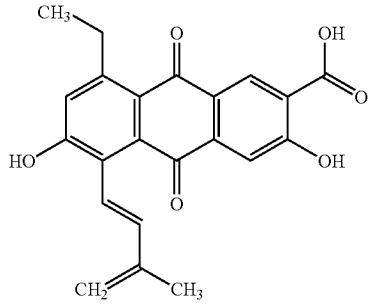

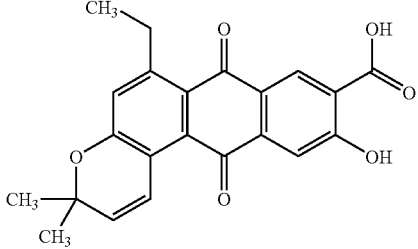

Accordingly, formulae Ia and Ib specifically describe 8-ethyl-3,6-dihydroxy-5[(1E)-3-methyl-1,3-butadienyl]-9,10-dioxo-9,10-dihydroanthracene-2-carboxylic acid and 6-ethyl-10-hydroxy-3,3-dimethyl-7,12-dihydro-3H-naphtho[2,3-f]chromene-9-carboxylic acid, respectively.

In the biosynthetic product the colouring substance can be present in association with ammonium, potassium or sodium cations, which can be present in excess. As accessories, substances of a protein character (amino acids, peptides) from the initial nutrient broth can be present in these products.

In order to obtain the red colorant it is possible to perform the cultivation of the productive strain in liquid nutrient broths by common methods, for example by the surface method in dishes or plates or by means of the submerged method in fermenters. The quantity of the inoculated material is 3 to 7% by volume. For the inoculation, operational bunches with five-day cultures incubated, e.g., in the cabbage infusion, in corn or yeast extracts or in the yeast autolysate are used.

Optimal conditions for conducting the process of the microbiological synthesis include temperatures of 27 to 29°

C., continuous mixing with the peripheral velocities of 160 to 280 min$^{-1}$, supply of air in the proportions of 1.2 air volumes to 1.0 volume of the broth, a gauge pressure in the operational fermenter amounting to 50 to 80 kPa.

Already after fermenting the productive microorganism for 24 to 35 hours, the liquid above the culture becomes red, and the intensity of the red colour is at its maximum—dark cerise colour—after an incubation period of 64 to 72 hours.

As components of the broth there are used carbohydrates, various saccharides, polyhydric alcohols and hydrocarbons, and also wastes of sugar production—molasses—in the quantity of 10 to 20 g for 1 litre of water.

For supplying nitrogen, for example the corn extract, yeast autolysate or extract, and also compounds containing nitrogen in various forms (such as amino acids) at a quantity of nitrogen of 0.5 to 0.7 wt. % can be used.

A person skilled in the art will appreciate that this invention is not limited to the use of the above-described, especially preferable, strain *Penicillium oxalicum* var. *Armeniaca* CCM 8242, but that use of other strains or mutants of said microorganism, producing a red colorant, obtained by common methods, e.g. by irradiating with X-rays or with UV light or by action of a phage and the like are also covered by the concept and scope of the present invention.

After completion of the biosynthesis, the obtained red colorant can be isolated from the nutrient broth by common isolating methods. The fermentation broth can be, after separation of the biomass or without separating the biomass, subjected to ultra-filtration and then concentrated, by nano-filtration, into a concentrate having a content of 80 to 100 g/l of the colorant. Alternatively, the liquid is filtered or centrifuged off from the nutrient broth in order to separate the biomass. For precipitating the colorant, the liquid is acidified to a pH of 3.0 to 2.5. Acidifying can be made with any organic or inorganic acid, acceptable in the food production. Precipitation can be carried out with aluminium potassium sulphate $AlK_2(SO_4)_3$. After the precipitation, the colorant is separated from the liquid, e.g. by centrifuging or filtering off.

In analytical evaluation, thus isolated product shows the following characteristics.

The colorant is a dark red to black powder, which is soluble in alkaline water at a pH of 8 to 9 ($NH_3$), in glacial acetic acid, in the egg white, in ethanol, in methanol, in butanol, partly in acetone, and insoluble in hexane, in ether, in benzene, in tetrachloromethane, and it forms water-insoluble chelates with metals.

The prepared solutions are raspberry red to dark red, stable in the pH values of 9 to 4 and they do almost not change their tone in dependence of the pH value. The coloration of a neutral solution does not change (unlike with carmine, betanine, anthocyane) even upon boiling of the solution for 30 minutes. The water solubility is approximately 100 g/l.

In assessing chemical purity, the following values have been found in the obtained product (in weight %):

| | | Evaluation method |
|---|---|---|
| Chemical purity: | | |
| Dry matter | not less than 85% | gravimetry |
| Coloured substances content | not less than 52% | spectrometry |
| Ash | not more than 12% | gravimetry |
| α-amino nitrogen | not more than 2.7% | formol titration |

| | | Evaluation method |
|---|---|---|
| Heavy metals: | | |
| arsenic | not more than 3 mg/kg | AAS |
| lead | not more than 10 mg/kg | AAS |
| mercury | not more than 1 mg/kg | AAS |
| cadmium | not more than 1 mg/kg | AAS |
| Mycotoxins: | | |
| aflatoxins (sum of $B_1$, $B_2$, $G_1$, $G_2$) | not more than 10 µg/kg | HPLC-FLD |
| ochratoxin A | not more than 20 µg/kg | HPLC-FLD |
| sterigmatocystin | not more than 10 µg/kg | TLC-fluoresc. |
| T-2 toxin | not more than 50 µg/kg | GLC-ECD |
| secalonic acid | not more than 12.5 µg/kg | HPTLC |
| Antibiotic activity: | absent | Codex Alimentarius |
| Microbial purity: | | |
| total number of bacteria | not more than 5000/g | |
| total number of fungi | not more than 100/g | |
| Salmonella | absent in 25 g sample | |
| *Escherichia coli* | absent in 10 g sample | |

The red colorant, isolated under the above-described conditions and having the above-mentioned characteristics, was subjected to test of acute oral toxicity, 90-day subchronical toxicity, acute dermal/eye irritation, antibiotic activity, cytotoxicity, mutagenicity and anti-cancer activity.

Acute Oral Toxicity:

In an acute oral toxicity test in mice, made in accordance with OECD Guidelines for testing chemicals, no toxic effects and no exits of animals were observed after a single dose of 2 g/kg of body weight.

Subchronical Toxicity:

In a 90-day subchronical toxicological study in rats in accordance with OECD Guidelines No. 408, the tested colorant was administered to the total of 120 SPF Han: Wistar rats in doses of 0.5, 10.0 and 25.0 mg/kg daily for 90 days. Administration was made per os, by gavage. In subsequent histopatological examination no changes ascribable to the substance tested have been found; neither hepatotoxic nor nephrotoxic effects have been found. In haematological examination the substance tested has not proved to be haematotoxic and in biochemical examination, the substance tested has not proved any marked effect on the biochemical parameters monitored.

Dermal/Eye Irritation:

The acute dermal irritation/corrosion test was performed in accordance with OECD Guidelines No. 404 and no acute irritating effects have been found. No signs of irritation or corrosion have been observed until 48 hours following the administration. The acute eye irritation/corrosion test was performed in accordance with OECD Guidelines No. 405. The red colorant has showed moderate effects in acute eye irritation/corrosion test (in the conjunctiva only); no signs have been observed after 72 hours following the administration.

Antibiotic Activity:

The tested substance was tested in bacterial strains *Staphylococcus aureus*, *Escherichia coli*, *Bacillus cereus*, *Bacillus circulans*, *Streptococcus pyogenes* and *Serratia marcescens* in three parallel runs for each strain (18 Petri dishes in total). No growth inhibition was observed around the applied disc in any of the dishes, not even in those kept at lowered temperature for 16 hours before the 24-hour cultivation itself (which should have improved the manifestation of substances slowly migrating in the agar).

Cytotoxicity:

Cytotoxicity was evaluated in a standard micronucleus test in mice. The red colorant, administered in a single per os dose of 2, 15 and 50 mg/kg, has not shown any cytotoxic effect. The numbers of micronuclei in erythrocytes have not increased following the administration. The substance tested has not shown any mutagenic effect.

Mutagenicity:

The mutagenicity test (Ames Reverse Mutation Test) was performed in histidine auxotrophic strains of Salmonella typhimurium in accordance with OECD Guidelines No. 471. Under the given conditions no effect of the product on mutation of bacteria has been observed.

Anti-Cancer Activity:

The red colorant isolated under the above-described conditions and having the above-mentioned characteristics was subjected to a screening study for anti-cancer properties.

The tested substance was administered to mice suffering from the ascitic form of Gardner lymphosarcoma (IP-LsG). 6-(2-(2-hydroxyethyl)aminoethyl)-5,11-dioxo-5,6-dihydro-11H-indeno[1,2-c]isoquinoline hydrochloride having the summary formula $C_{20}H_{18}N_2O_3 \cdot HCl$ was used as a reference substance.

Female $C_3H$ mice weighing 26.1 to 27.3 g were used. The animals were kept in plastic containers and fed with the NOE diet made by RATIO, s.r.o., Břeclav, Czech Republic, and with potable water ad libitum. The temperature in the room was maintained, the relative humidity was 60%, and the light regimen was not regulated.

The Gardner lymphosarcoma is maintained in the ascitic form in the $C_3H$ mice by inoculating ascitic cells removed a week after the previous inoculation by puncturing the abdominal cavity. The mice are administered with 0.2 ml of the ascites diluted with an isotonic solution of sodium chloride for injections intraperitoneally 10 to 20 times. The cell material for tests is obtained by puncturing the abdominal cavity on the seventh day following inoculation. For the therapeutic test, the inoculation with the ascites diluted with an isotonic solution of sodium chloride for injections was made by administering $10^7$ cells in a volume of 0.2 ml i.p. to each animal.

The $C_3H$ mice were over 6 weeks old, weighing 26.1 to 27.3 g, in groups of 10 animals, the control was-common. Two dosage groups were used for each route of administration and for one substance tested.

The dosage levels: 200 and 100 mg/kg×5 p.o. and 100 and 50 mg/kg×5 s.c. in a volume 0.2 to 0.4 ml and 0.2 to 0.4 ml p.o. (reference substance), resp. for 20 g body weight. Frequency of administration: 1× daily beginning on the first day. The tested substance was administered in a continuous pattern on the $1^{st}$ to $5^{th}$ days in doses given in Table 1 and the reference substance was administered p.o. once on the $1^{st}$ day.

After the administration was finished, the animals were left for monitoring the survival time. The dose dependence of the survival time was evaluated in comparison with the non-administered control. Time as a biological response was currently evaluated by means of the non-parametric test according to Hájek (Fabián V.: Základní statistické metody ("Basic Statistical Methods"), NČSAV, Prague 1963).

After the experiment was complete, time in case of point estimates was evaluated using the test of identity of two means (Student t-test) under the presumption of logarithmic-normal distribution of time values and under the presumption of various unknown variances (Roth Z., Josífko M., Malý V., Trčka V.: Statistické metody v experimentální medicíně ("Statistical Methods in Experimental Medicine"); p. 278, SZN, Prague 1962). Geometrical averages were calculated from the individual values of time to death. The differences In average values in which the value of the test criterion has exceeded the critical value for the significance level of 5% were designated as statistically significant.

The results are summarized in the following tables:

TABLE 1

The table illustrates medians of the time to death, statistical significance as evaluated by means of the non-parametric test according to Hájek at the significance level $\alpha = 0.05$ and values of the number of surviving animals related to the initial value in dependence of doses of the substances.

| substance | dose mg/kg/day | n (j) | median of time to death (days) | survival LTS | note |
|---|---|---|---|---|---|
| control | 0 | 10 | 14.0 | 0/10 | |
| red colorant | 200 p.o. | 10 | 15.0 | 1/10 | |
| lot 290698 | 100 p.o. | 10 | 14.0 | 0/10 | |
| | 100 s.c. | 10 | 13.0 | 0/10 | 1) |
| | 50 s.c. | 10 | 13.0 | 0/10 | |
| referenční | 200 p.o. | 10 | >65.0 | 10/10 | 1) |
| | 100 p.o. | 10 | >48.5 | 5/10 | 1) | n - number of animals in a group
1) statistically significant difference against the control at the significance level $\alpha = 0.05$
LTS - number of animals surviving on day 65

TABLE 2

The table illustrates average survival times, reliability limits for the geometrical average for $P = 1 = \alpha = 0.95$ and relative values of average survival time in % of the control in dependence of doses of the substances.

| substance | dose mg/kg/day | n (j) | geom. average (days) | reliability limits (days) | survival (% of control) | note |
|---|---|---|---|---|---|---|
| control | 0 | 10 | 14.05 | /12.6; 15.7/ | 100 | |
| red colorant | 200 p.o. | 10 | >17.50 | /12.5; 24.6/ | >125 | |
| lot 290698 | 100 p.o. | 10 | 14.33 | /13.3; 15.4/ | 102 | |
| | 100 s.c. | 10 | 12.87 | /12.3; 13.5/ | 92 | |
| | 50 s.c. | 10 | 13.86 | /11.9; 16.2/ | 99 | | n - number of animals in a group

TABLE 3

The table illustrates average weights of the animals in the beginning of the experiment and coefficients of weight loss in comparison with the control group in dependence of dosage of the substances one week after the start of the therapy.

| substance | dose mg/kg/day | n (j) | arith. average of weight (g) | weight coefficient (%) | note |
|---|---|---|---|---|---|
| control | 0 | 10 | 26.1 | 0.00 | |
| red colorant | 200 p.o. | 10 | 27.2 | −5.00 | |
| lot 290698 | 100 p.o. | 10 | 27.2 | −5.00 | |
| | 100 s.c. | 10 | 27.3 | −5.99 | |
| | 50 s.c. | 10 | 26.7 | −1.60 | |
| reference | 200 p.o. | 10 | 26.7 | −14.63 | |
| | 100 p.o. | 10 | 26.1 | −6.67 | | n - number of evaluated animals in a group

It can be judged based on the results set forth in the above tables that the optimal dose can be found near the highest tested dose of 200 mg/kg p.o.×5, i.e. at about the cumulative dose of 1 g/kg p.o. From the difference in behaviour of the activity curves in the oral and subcutaneous administrations, metabolic transformation of the substance in liver can be anticipated. Under the presumption of intensive metabolization, a repeated dose of 600 mg/m² p.o. can be estimated as tolerable for man. This dose corresponds to 16.2 mg/kg p.o., which corresponds to a repeated daily dose of 1135 mg p.o.×5, i.e. to a cumulative dose of 5.67 g p.o. in a human weighing 70 kg. The substance tested does not appear to be toxic since its administration is associated with weight losses lower than 10%, especially in comparison with the reference substance.

BRIEF DESCRIPTION OF THE DRAWING

The activity curve in FIG. 1 represents the function of the natural logarithm of the relative risk index R in dependence of the dose of the substance in various routes of administration.

EXAMPLES

Example 1

Figure 1:
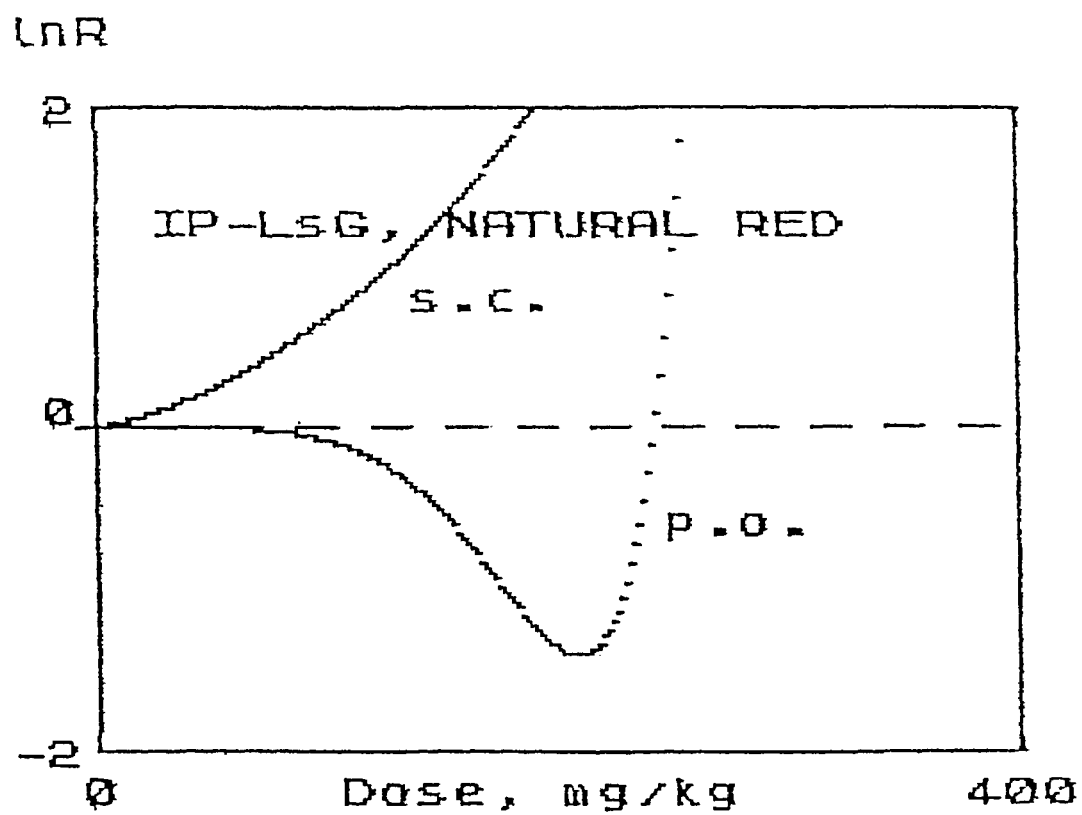

A broth, comprising 12 g/l of granulated sugar, 5 g/l of corn extract, 0.002 g/l of zinc sulphate and 0.001 g/l of magnesium sulphate, is inoculated with a two-day culture of *Penicillium oxalicum* var. *Armeniaca* CCM 8242, which has been cultivated in an inoculation device, in an amount of 4 vol. % based on the broth. After the biosynthesis of the red colorant is completed, the liquid from the broth is centrifuged off for being separated from the biomass. The liquid is acidified to pH 3.0 to 2.5 with acetic acid. Precipitation with aluminium potassium sulphate $AlK_2(SO_4)_2$ is performed. Following the precipitation, the colorant is separated from the liquid by centrifugation.

Example 2

A broth, comprising 16 g/l of granulated sugar, 7 g/l of yeast extract, 0.002 g/l of zinc sulphate and 0.001 g/l of magnesium sulphate, is inoculated with a two-day culture of *Penicillium oxalicum* var. *Armeniaca* CCM 8242, which has been cultivated in an inoculation device, in an amount of 6 vol. % based on the broth. After the biosynthesis of the red colorant is completed, the liquid from the broth is centrifuged off for being separated from the biomass. The liquid is acidified to pH 3.0 to 2.5 with citric acid. Precipitation with aluminium potassium sulphate $AlK_2(SO_4)_2$ is performed. Following the precipitation, the colorant is separated from the liquid by centrifugation and re-crystallized.

Example 3

A broth, comprising 20 g/l of granulated sugar, 10 g/l of yeast autolysate, 0.002 g/l of zinc sulphate and 0.001 g/l of magnesium sulphate, is inoculated with a two-day culture of *Penicillium oxalicum* var. *Armeniaca* CCM 8242, which has been cultivated in an inoculation device, in an amount of 8 vol. % based on the broth. After the biosynthesis of the red colorant is completed, the broth is subjected to ultra-filtration using 10000 to 20000 μm membranes, followed by concentrating by means of nano-filtration using 200 to 500 μm membranes to a concentrate containing 100 g/l of the colorant.

Example 4

A broth, comprising 18 g/l of granulated sugar, 19 g/l of yeast extract, 0.002 g/l of zinc sulphate-and 0.001 g/l of magnesium sulphate, is inoculated with a two-day culture of *Penicillium oxalicum* var. *Armeniaca* CCM 8242, which bas been cultivated in an inoculation device, in an amount of 8 vol. % based on the broth. After the biosynthesis of the red colorant is completed, biomass is centrifuged off from the broth and the liquid is subjected to ultra-filtration using 10000 to 20000 μm membranes, followed by concentrating by means of nano-filtration using 200 to 500 μm membranes to a concentrate containing 80 g/l of the colorant.

Example 5

25 g of the concentrate obtained according to Example 3 is homogenized with 75 g of maltodextrin and dried in a spray drier at 180 to 220° C.

Example 6

65 g of the concentrate obtained according to Example 3 is homogenized with 35 g of starch and dried in a spray drier at 180 to 220° C.

Products obtained according to Examples 1 to 6 can be added to food products such as sausages, confectionery, yoghurts, soft and alcoholic drinks and the like in amounts of 50 to 400 mg/kg based on the food product. They can be further used for preparing aqueous, spirituous or aqueous-spirituous solutions, having the active substance concentrations of 2 to 10 vol. %.

Example 7

The crystalline product, obtained according to Example 2, is homogenized with a pharmaceutical excipient having the form of an emulsion, homogenized with lactose and compressed into tablets having the active substance contents of 350 and 450 mg. Tablets can be prepared also with glucose and other pharmaceutically acceptable carriers.

The invention claimed is:

1. A pharmaceutical composition in the form of a tablet, a capsule, a pill or an emulsion comprising
   (a) an active substance comprising 20% to 99.99% by weight of a product of biosynthesis of *Penicillium oxalicum* var. *Armeniaca* CCM 8242, wherein the product is made by a method comprising the following steps:
   (i) innoculating a nutrient broth comprising carbohydrates and ammonia nitrogen, wherein the nutrient broth comprises 12 g/l of granulated sugar, 5 g/l of corn extract, 0.002 g/l of zinc sulphate and 0.001 g/l of magnesium sulphate, with a two-day culture of *Penicillium oxalicum* var. *Armeniaca* CCM 8242, in an amount of 4 vol. % based on the broth;
   (ii) culturing the inoculant of (i) until biosynthesis of a red colorant is detected;
   (iii) centrifuging off the liquid from the broth and separating it from the biomass;
   (iv) acidifying the liquid of (iii) to about pH 3.0 to 2.5 with an acid;
   (v) precipitating with aluminium potassium sulphate $(AlK_2(SO_4)_2)$; and
   (vi) separating the product from the liquid by centrifugation or by filtering,
   wherein the separated product has the following properties: is soluble in alkaline water at a pH of about 8 to 9, glacial acetic acid, ethanol, methanol or butanol; is insoluble in hexane, ether, benzene or tetrachloromethane; forms a water-insoluble chelate with metals; has biological activity comprising an anti-lympho-carcinoma anti-cancer effect; and (b) 0.01 to 80% by weight of a physiologically inert and pharmaceutically acceptable carrier.

2. A pharmaceutical composition in the form of a tablet, a capsule, a pill or an emulsion comprising an active substance comprising an anthraquinone structure, wherein the structure is represented by formula I

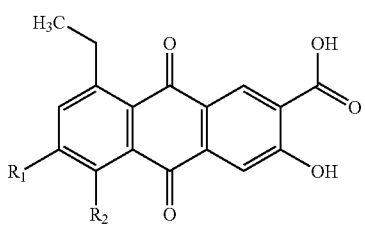

wherein $R_1$, is hydroxy and $R_2$ is 3-methyl-1,3-butadienyl, and wherein optionally $R_1$, and $R_2$ are cyclized through the oxygen atom of the hydroxy.

3. The pharmaceutical composition of claim 1, wherein the product of biosynthesis comprises 8-ethyl-3,6-dihydroxy-5[(1E)-3-methyl-1,3-butadienyl]-9,10-dioxo-9,10-dihydroanthracene-2-carboxylic acid.

4. The pharmaceutical composition of claim 1, wherein the product of biosynthesis comprises 6-ethyl-10-hydroxy-3,3-dimethyl-7,12-dihydro-3H-naphtho [2,3f]chromene-9carboxylic acid.

5. The pharmaceutical composition of claim 1 wherein said carrier comprises 11 to 75 weight % maltodextrin.

6. The pharmaceutical composition of claim 1 wherein said carrier comprises 30 to 40 weight % starch.

7. The pharmaceutical composition of claim 1, formulated in a unit dosage form.

8. The pharmaceutical composition of claim 1 in the form of an emulsion, a tablet, capsule or pill.

9. The pharmaceutical composition of claim 1 wherein said carrier comprises a physiologically acceptable liquid.

10. A tablet, a capsule, a pill or an emulsion comprising the pharmaceutical composition of claim 1 or claim 2.

11. A method of treating a lymphosarcoma comprising administering a pharmaceutically acceptable amount of the pharmaceutical composition of claim 1 or claim 2 to a subject.

12. A method of treating a Gardner lymphosarcoma comprising administering the pharmaceutical composition of claim 1 or claim 2, to an individual in need thereof.

13. The pharmaceutical composition of claim 2, further comprising a carrier comprising 11 to 75 weight % maltodextrin.

14. The pharmaceutical composition of claim 2, further comprising a carrier comprises 30 to 40 weight % starch.

15. The pharmaceutical composition of claim 2 in a unit dosage form.

16. The pharmaceutical composition of claim 2 in the form of a tablet, capsule or pill.

17. The pharmaceutical composition of claim 2 wherein said carrier comprises a physiologically acceptable liquid.

18. A pharmaceutical composition comprising a crystalline product homogenized with a pharmaceutical excipient having the form of an emulsion, homogenized with lactose and compressed into tablets wherein the product comprises the pharmaceutical composition of claim 2.

19. A method of treating a lymphosarcoma comprising administering a pharmaceutically effective amount of the composition of claim 18 to a subject.

20. A method of treating a lymphosarcoma comprising administering the composition of claim 18 to an individual in need thereof.

21. A pharmaceutical composition comprising 8-ethyl-3,6-dihydroxy-5[(1E)-3-methyl-1,3-butadienyl]-9,10-dioxo-9,10-dihydroanthracene-2-carboxylic acid formulated as a pharmaceutical in the form of a tablet, a capsule, a pill or an emulsion.

22. A pharmaceutical composition comprising 6-ethyl-10-hydroxy-3,3-dimethyl-7,12-dihydro-3H-naphtho[2,3-f]chromene-9 carboxylic acid formulated as a pharmaceutical in the form of a tablet, a capsule, a pill or an emulsion.

23. The pharmaceutical composition of claim 1, wherein the product comprises a structure represented by formula I

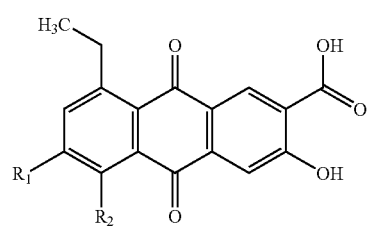

wherein $R_1$, is hydroxy and $R_2$ is 3-methyl-1,3-butadienyl, and wherein optionally $R_1$, and $R_2$ are cyclized through the oxygen atom of the hydroxy.

24. The pharmaceutical composition of claim 18, claim 21 or claim 22, further comprising a pharmaceutically acceptable excipient.

25. The composition of claim 24, wherein the composition is formulated in a crystalline form, or formulated as an isotonic solution of sodium chloride for injection, an emulsion, a pill or a tablet.

26. The pharmaceutical composition of claim 1, claim 2, claim 21 or claim 22, wherein the composition is formulated in a unit dosage form.

27. The pharmaceutical composition of claim 1, wherein the method for making the product further comprises crystallizing the separated product.

28. The pharmaceutical composition of claim 1, wherein the method for making the product further comprises ultra-filtration of the separated product, or ultra-filtration followed by nano-filtration of the separated product.

29. A pharmaceutical composition comprising the composition of claim 1 or claim 2 compressed into tablets having the active substance contents of 350 or 450 mg, or, formulated an amount of between about 50 to 400 mg/kg, or at a concentration of between about 2 to 10 vol. %.

30. A pharmaceutical composition comprising the pharmaceutical composition of claim 21 formulated an amount of between about 50 to 400 mg/kg, or at a concentration of between about 2 to 10 vol. %.

31. A pharmaceutical composition comprising the composition of claim 22 formulated an amount of between about 50 to 400 mg/kg, or at a concentration of between about 2 to 10 vol. %.

32. The pharmaceutical composition of claim 18, claim 30 or claim 31, wherein the composition or product is in an amount of between about 50 to 400 mg/kg, or is at a concentration of between about 2 to 10 vol. %.

33. A method of inhibiting the formation of or treating a lymphosarcoma comprising administering a pharmaceutically effective amount of the pharmaceutical composition of claim 31 or claim 32 to a subject.

34. A method of treating a lymphosarcoma comprising administering a pharmaceutically effective amount of the pharmaceutical composition of claim 21 to a subject.

35. A method of treating a lymphosarcoma comprising administering a pharmaceutically effective amount of the pharmaceutical composition of claim 22 to a subject.

36. A method of treating a lymphosarcoma comprising (a) administering the pharmaceutical composition of claim 1 or claim 2, and (b) supplementing the treatment with a nutritional supplement comprising the composition of claim 1 or claim 2.

37. A method of treating a lymphosarcoma comprising (a) administering the pharmaceutical composition of claim 18 or claim 21, and (b) supplementing the treatment with a nutritional supplement comprising the composition of claim 18 or claim 21.

38. A method of treating a lymphosarcoma comprising (a) administering the pharmaceutical composition of claim 22, claim 30 or claim 31, and (b) supplementing the treatment with a nutritional supplement comprising the composition of claim 22, claim 30 or claim 31.

39. The composition of claim 1, claim 2, claim 21 or claim 22, wherein the pharmaceutical composition is formulated in a unit dosage form comprising tablets having active substance contents of about 350 to 450 mg.

40. A pharmaceutical composition in the form of a tablet, a capsule, a pill or an emulsion, comprising
(a) a product of biosynthesis of *Penicillium oxalicum* var. Armeniaca CCM 8242, wherein the product is made by a method comprising the following steps:
 (i) innoculating a nutrient broth comprising carbohydrates, ammonia nitrogen, zinc sulphate and magnesium sulphate with *Penicillium oxalicum* var. Armeniaca CCM 8242;
 (ii) culturing the inoculant of (i) until biosynthesis of a red colorant is detected;
 (iii) centrifuging off the liquid from the broth and separating it from the biomass;
 (iv) acidifying the liquid of (iii) to about pH 3.0 to 2.5 with an acid;
 (v) precipitating with aluminium potassium sulphate ($AlK_2(SO_4)_2$); and
 (vi) separating the product from the liquid by centrifugation or by filtering,
 wherein the separated product has the following properties: is soluble in alkaline water at a pH of about 8 to 9, glacial acetic acid, ethanol, methanol or butanol; is insoluble in hexane, ether, benzene or tetrachloromethane; forms a water-insoluble chelate with metals; and
(b) a pharmaceutically acceptable or physiologically inert carrier.

41. The pharmaceutical composition of claim 40, wherein the composition is formulated in a crystalline form, or formulated as an isotonic solution of sodium chloride for injection, an emulsion, a pill or a tablet.

42. The pharmaceutical composition of claim 40, wherein the composition is formulated in a unit dosage form.

43. The pharmaceutical composition of claim 40, wherein the method for making the product further comprises crystallizing the separated product.

44. The pharmaceutical composition claim 40, wherein the method for making the product further comprises ultra-filtration of the separated product, or ultra-filtration followed by nano-filtration of the separated product.

45. A method of treating lymphosarcoma comprising administering a pharmaceutically effective amount of the composition of claim 40 to a subject.

* * * * *